United States Patent [19]

Cheetham et al.

[11] Patent Number: 5,077,206
[45] Date of Patent: Dec. 31, 1991

[54] PROCESS FOR PREPARING L-RHAMNOSE

[75] Inventors: Peter S. J. Cheetham, Ashford; Michael A. Quail, Sheffield, both of Great Britain

[73] Assignee: Unilever Patent Holdings B.V., Rotterdam, Netherlands

[21] Appl. No.: 273,782

[22] Filed: Nov. 21, 1988

[30] Foreign Application Priority Data

Nov. 20, 1987 [GB] United Kingdom ............... 8727223

[51] Int. Cl.$^5$ ..................... C12P 19/14; C07G 17/00; C12N 9/24; C07H 15/00
[52] U.S. Cl. ........................................ 435/99; 435/74; 435/75; 435/105; 435/267; 435/274; 435/942; 435/922; 435/853; 435/873; 435/256; 435/190; 435/138; 536/8; 536/4.1; 536/128
[58] Field of Search ..................... 435/99, 74, 75, 105, 435/267, 274, 942, 922, 853, 873, 256, 190, 138; 536/8, 4.1, 128

[56] References Cited

U.S. PATENT DOCUMENTS

| | | | |
|---|---|---|---|
| 2,950,974 | 8/1960 | Smythe et al. | 536/8 |
| 3,651,221 | 3/1972 | Conrad et al. | 435/190 |
| 3,885,949 | 5/1975 | Ono | 71/79 |

OTHER PUBLICATIONS

Patent Abstracts of Japan, vol. 4, No. 93 (C-17) [575], Jul. 5, 1980.

Primary Examiner—Johnnie R. Brown
Assistant Examiner—Pamela S. Webber
Attorney, Agent, or Firm—Cushman, Darby & Cushman

[57] ABSTRACT

The invention provides a process for preparing L-rhamnose by hydrolyzing a rhamnosidic bond of a glycoside having rhamnose in a terminal position, by enzymatically hydrolyzing the glucoside with an enzyme combination comprising biological structural material degrading enzyme and a naringinase preparation which has a higher rhamnosidase activity than beta-glucosidase activity. Preferably the enzyme combination having rhamnosidase activity together with additional enzyme activity is a selected partially purified enzyme preparation having high rhamnosidase activity and low glucosidase activity together with biological structural material degrading activity. More preferably the additional enzyme activity is derived from an enzyme of the group consisting of protease, lipase, pectinase, cellulase and hemicellulase.

13 Claims, 1 Drawing Sheet

GRAPH 1: HNP HYDROLYSIS OF CITRUS WASTE

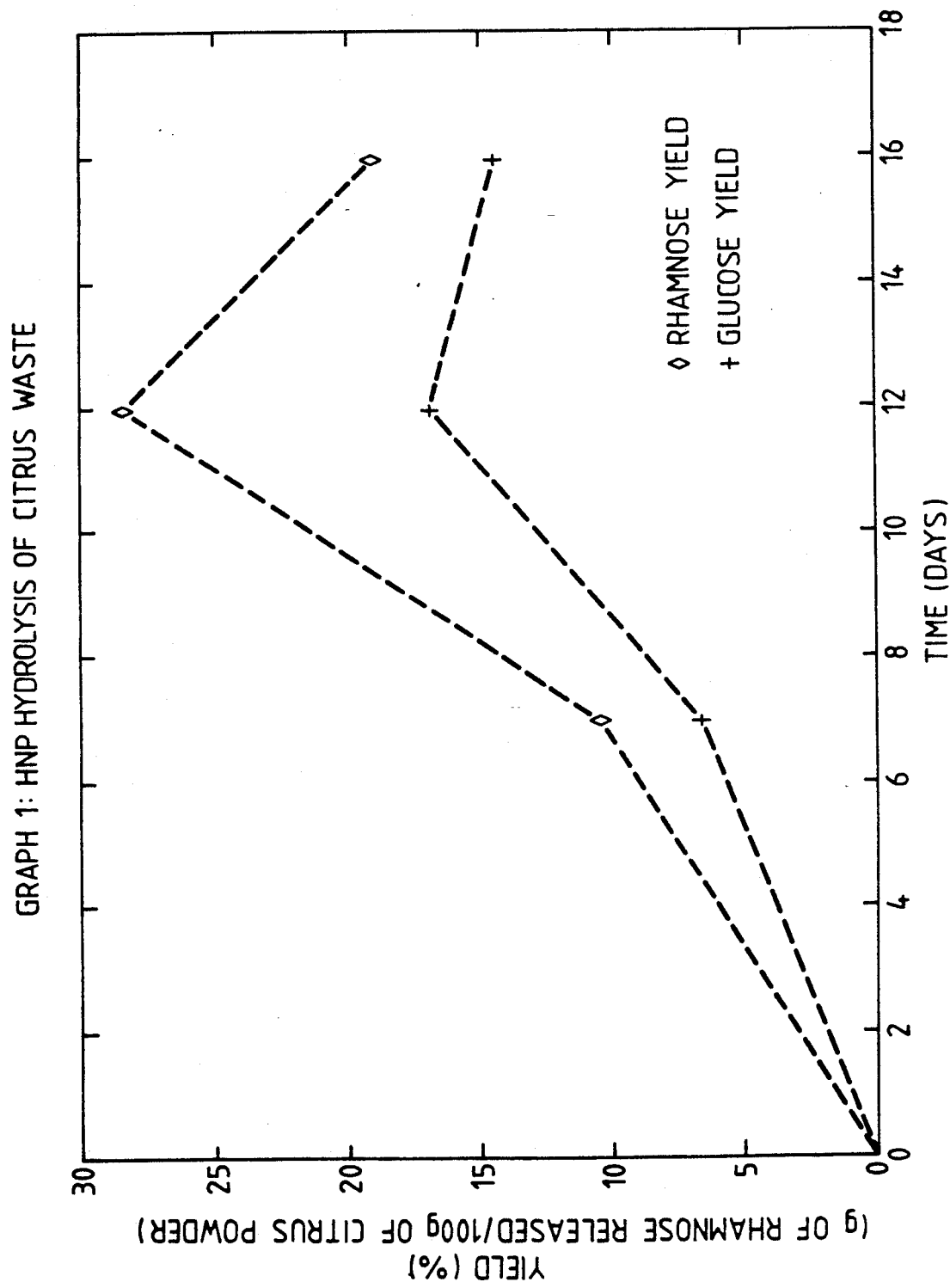

PROCESS FOR PREPARING L-RHAMNOSE

The invention relates to a process for preparing L-rhamnose by hydrolysing a rhamnosidic bond of a glycoside having rhamnose in a terminal position by enzymic reaction.

Such a process to obtain free L-rhamnose from glycoside material is known from the prior art. Japanese patent application (JP-A-)62/293 (Kanegafuchi Chem.Ind.Co) discloses hydrolysing flavonoid glycosides like hesperidin, naringin, neohesperidin, rutin, linarin, poncerin or quercitrin by the action of an enzyme selectively cleaving the rhamnosidic bond (rhamnosidase) and recovering L-rhamnose from the hydrolysate. The enzyme employed was commercially available naringinase (a mixture of rhamnosidase and beta-glucosidase) or hesperidinase prepared by purifying the culture liquid of certain microorganisms of the Aspergillus or Penicillium genus. This known process has the disadvantages that it requires the enzyme purified rhamnosidase as well as relatively pure flavonoid glycoside starting material.

BRIEF DESCRIPTION OF THE DRAWING

FIG. 1 is the graph of the HNP hydrolysis of citrus waste, wherein the yield (g of rhamnose released/100 g of citrus powder) is shown as a function of time.

According to the present invention especially an impure source thereof is selectively enzymically hydrolysed by using an enzyme combination comprising enzymes capable of degrading biological structural material such as protease, lipase, pectinase, cellulase and hemicellulase in addition to the rhamnosidase. It will be appreciated that most commercially available grades of rhamnosidase active towards naringin, hesperdin, neohesperidin, etc. contain appreciable amounts of beta glucosidase and consequently according to the present invention such enzyme preparations are employed which are high in rhamnosidase. Suitable enzyme preparations that contain enzyme activity capable of degrading biological material as specified above and rhamnosidase can be obtained by mixing commercially available purified enzymes or by judicious selection of available enzyme preparations which have not been purified or are partially purified. Also crude culture liquids of certain microorganisms have been found useful.

The use of these enzyme combinations also has the advantage that, it causes the precipitation of impurities so facilitating purification of the hydrolysate and also permits the use of cheap impure glycoside materials such as crude citrus material as well as the purified flavonoid material which require degradation to make the glycosides available to the rhamnosidase which contain a variety of rhamnose containing flavonoid glycosides, such as naringin, hesperidin, neohesperidin etc. used so far.

Crude citrus, material from orange or grapefruit peel or waste from juice pressing is a particularly good starting material for the process according to the present invention. For instance dried samples of sweet orange peel and in particular bitter green orange segments which have a higher glycoside content could be ground to a powder and then used in a 5 to 10% (D.w./w) suspension in water and then incubated with a combination of biological structural material degrading enzyme and rhamnosidase. The glycoside starting material having rhamnose in a terminal position which can be used according to the present invention can be purified plant materials, such as rutin or naringin but preferably crude plant material containing the rhamnose containing flavonoid glycosides, such as citrus material (in particular crude material derived from unripe citrus fruit, gum arabic), fenugreek, microbial rhamnolipids or microbial rhamnopolysaccharides e.g. polyrhamnose. Microorganisms capable of producing extracellular rhamnosidase were isolated by deliberately contaminating areas of garden soil with naringin over a period of months, and then plating out samples of this soil on agar plates containing naringin as a sole carbon source. Any microbial colonies that grew were thus capable of producing the required rhamnosidase. If glucose is also liberated during the enzymatic degradation of the glycoside it can be fermented out preferably as it is formed by a suitable yeast (e.g. bakers yeast in an amount of 1 g per 100 g of glycoside material) or enzymically e.g. by action of e.g. glucose oxidase optionally in combination with catalase and then removed as the calcium salt of gluconic acid. Also it was a convenient route to convert any such glucose into 5-ketogluconic acid which is then removed The latter oxidation is conveniently effected by *Gluconobacter oxydans* followed by removal of 5-ketogluconic acid by precipitation and filtration, leaving a substantially pure rhamnose syrup. Optionally glucose and rhamnose may be separated by adsorption techniques, e.g. using charcoal to preferentially adsorb the rhamnose.

The hydrolysate obtained as described above contains rhamnose usually together with some glucose and some flavones and flavone glycosides and is preferably further purified so as to remove the glucose the flavone and flavone glycosides. Convenient methods for this are:

1. Selective fermenting out of glucose with a suitable microorganism, under conditions chosen to preferentially ferment glucose, rather than rhamnose; ethanol being produced as a side product. Suitable microorganisms are e.g. *Saccharomvces cerevisiae, Candida albicans, Lactobacillus delbruckii* and *Proteus buloaris*. Preferably, the fermentation is carried out at a pH between 4 and 4 5. Selective fermentation was inhibited when the pH of the syrup was higher e.g. pH 6.0. Preferably also the microorganism, in particular a yeast has been immobilized e.g. in calcium alginate which can optionally be dried prior to use to improve their mechanical and storage properties, and the hydrolysate is pumped through a column packed with immobilized microorganisms. In addition free cells or immobilized cells can be used in a stirred batch reaction. The activities are for free cells batchwise 1.9 and 3.4 gram of glucose free rhamnose per liter of reactor per hour respectively; for the immobilized cells used glucose free rhamnose/liter/h in a column 22.4 units. Most of the rhamnose lost was metabolised during the start of the fermentation. Varying the sugar concentration had no effect on the yield of rhamnose, which is about 65% when all the glucose has been removed, but the presence of lower glucose concentrations result in a proportionally lower fermentation time, therefore a proportionally higher flow rate can be used. Higher yields of rhamnose were obtained if some residual glucose was tolerated e.g. 74%, 82% and 92.5% recoveries of rhamnose respectively at 1%, 2% and 6% (w/w) residual glucose. The immobilized cells can be re-used but their activity decreases with time.

2. Alternatively glucose may be removed by the selective enzymic oxidation of glucose to gluconic acid (using glucose oxidase and catalase), which is subsequently precipitate as its calcium salt and removed. The glucose oxidase catalase may also be used in an immobilized form sources of the enzyme that are most resistant to inhibition by product are preferred. The time at which the calcium source is added is not critical, indeed it can be present with the glucose/catalase from the start to precipitate gluconic acid as it is formed although this option is not preferred. Glucose dehydrogenase may also be used instead of glucose oxidase. Recoveries of rhamnose of up to 100% can be obtained by this method whilst completely removing the glucose. Gluconic acid is produced as a side-product from the glucose.

3. Selective oxidation of glucose to 5-ketogluconic acid by means or a suitable microorganism and separate recovery of 5-ketogluconic acid and rhamnose. One preferred microorganism for carrying out this oxidation is Gluconobacter oxydans. This method, however, does not work if the glucose concentration in solution is above 6-7% (w/v) since glucose is inhibitory at high concentrations. Therefore only dilute sugar solutions can be successfully treated by this method. Nevertheless recoveries of rhamnose, free of glucose, of up to 95% were obtained by this method. Also the calcium salt of 5-ketogluconic acid is produced as a side-product.

4. Selective adsorption/absorption of either the glucose or the rhamnose e.g. using activated charcoal or bone-charcoal to preferentially adsorb the rhamnose. This method is best carried out using the carbon in a chromatographic mode.

The hydrolysis of suitable glycoside material according to the present invention is preferably carried out at a temperature between 20° and 60° C., the pH of the incubated mixture is preferably kept between pH 2 and 8 and the incubation time generally lies between 30 minutes and 36 hours. The incubated mixture is then subjected to one or more purification steps. Usually the suspension is first cooled and the solid material is then removed e.g. by allowing to settle and decanting or by centrifugation, then any glucose also liberated during the incubation is removed as previously described and optionally further purification by adsorption/absorption follows. In particular treatment with polymeric material like polyvinylpolypyrrolidone (p.v.p.),ion exchange resin and/or activated charcoal proved beneficial. Optionally crystallization from the syrup can be carried out, yielding pure crystalline L-rhamnose.

The rhamnose so obtained was of high purity and a natural product, which is very suitable for further conversions to pharmaceutical and flavour compounds.

More in particular, this grade of rhamnose can be converted into natural flavour compounds such as 2,5-dimethyl-4-hydroxy-2,3-dihydrofuran-3-one.

The invention is illustrated by the following examples:

EXAMPLE 1

220 g of citrus powder (ex Zoster, Spain) mainly containing naringin and neohesperidin were suspended in 1 liter of water and then heated to 80° C. 1 ml of enzyme having rhamnosidase activity (TP 104A, ex Biocatalysts Pontypridd, U.K) supplemented with enzyme SP 249 (ex NOVO, Denmark) having plant structural material degrading activity was added and the solution incubated at 40° C. until according to hplc-analysis no further rhamnose was liberated. The selectivity of the reaction, i.e. the ratio of the rhamnose to glucose released was maximal over the pH range 4.8-5.6. The SP 24G enzyme further increased the amounts of rhamnose released and also the selectivity of the reaction. The mixture was allowed to settle and the supernatant was decanted and cooled to 4° C., whereby certain impurities were precipitated as an oily deposit which was removed. The supernatant was then treated with 10 g of polyvinylpolypyrrolidone (p.v.p.) to remove further impurities and the supernatant was then decolourized by adding 2 g of activated charcoal. Further purification was effected by treatment with Amberlite (tradename) XAD-4 resin (10 g).

The relatively small amount of glucose present in the decolourized supernatant was removed by incubating with yeast (S. cerevisiae) and the solution obtained proved to contain pure L-rhamnose (16 g). The rhamnose solution so obtained was subsequently crystallized to yield 14 g crystalline L-rhamnose.

EXAMPLES 2-10

Enzyme treatment of citrus waste powder, obtained from Zoster, Murcia, Spain containing 60% of naringin was treated with various enzyme preparations using the procedure described in Example 1. The enzymes and yields are tabulated below:

| Ex. | Enzyme | Yield of rhamnose (g/100 g powder) |
|---|---|---|
| 2 | Biopectinase L | 32.0 |
| 3 | Sigma naringinase | 31.4 |
| 4 | Hesperidinase I | 27.1 |
| 5 | High naringinase pectinase | 27.0 |
| 6 | Naringinase (Biocatalysts) | 23.5 |
| 7 | Biopectinase P | 19.5 |
| 8 | 1286 (Biocatalysts) | 10.6 |
| 9 | Pectinex | 7.5 |
| 10 | Biocon pectinase | 4.5 |

The TP enzymes are naringinase preparations in which the B-glucosidase component has been selectively inactivated for instance at 65° C. for 2 h prior to use.

EXAMPLES 11-27

Enzymic treatment of crude bitter or sweet orange peel, (whole and quarters ex Siber Hegner Ltd., Beckenham, Kent, Great Britain). Impure mixtures of enzymes, commercially available in bulk, were used to hydrolyse rhamnose (+glucose) from the flavonoid glycosides (mainly naringin, neohesperidin, etc.) present in orange wastes. These enzymes were supplemented with a biological structural material degrading enzyme cocktail to supplement the cellulase/hemicellulases/pectinases present in the impure naringinase enzymes so as to liberate the glycosides from the peel to so make the glycosides available for hydrolysis. Following reaction the hydrolysate was purified and the rhamnose recovered. The results are tabulated below:

| Ex. | enzymes added | Rha yield | Glu yield |
|---|---|---|---|
| | SWEET ORANGE PEEL | | |
| 11 | 1286 | 0.7% | 16.5% |
| 12 | 1286 + SP 249 | 1.2% | 17.9% |
| 13 | TP 104A | 0.3% | 14.5% |
| 14 | TP 104A + SP 249 | 0.8% | 15.8% |
| 15 | Biopectinase L | 0.3% | 19.1% |
| 16 | Biopectinae L + SP 249 | 0.6% | 20.2% |
| | BITTER ORANGE PEEL | | |
| 17 | 1286 | 3.0% | 4.4% |
| 18 | 1286 (heat) | 1.9% | 4.6% |
| 19 | 1286 + SP 249 | 3.7% | 9.6% |
| 20 | 1286 (heat) + SP 249 | 3.7% | 8.2% |
| 21 | TP 104A | 1.3% | 1.0% |
| 22 | TP 104A + SP 249 | 3.3% | 6.6% |
| 23 | Biopectinase L | 3.0% | 8.0% |
| 24 | Biopectinase L + SP 249 | 3.2% | 12.2% |
| 25 | Sigma Naringinase | 2.4% | 3.2% |
| 26 | Sigma Naringinase + SP 249 | 4.8% | 8.8% |
| 27 | TP 110 + SP 249 | 2.4% | 17.6% |

Other supplementary enzymes such as cellulose preparations showed a similar effect to the SP 249.

EXAMPLES 28-31

These examples describe the simultaneous treatment of a 20% (w/v) suspension of citrus waste powder ex Zoster, Murcia, Spain with hydrolytic enzymes indicated, followed by glucose removal procedures as described in the previous examples. The results are tabulated below:

| Ex. | Enzyme | Biocatalyst added | Rha yield (%) (g/100 g powder) | Glu yield (%) (g/100 g powder) |
|---|---|---|---|---|
| 28 | 1286 | S. cerevisiae | 15 | 11 |
| 29 | 1286 | glucose oxidase + catalase | 15.3 | 12.6 |
| 30 | 1286 | G. oxydans | 4.0 | 1.2 |
| 31 | 1286 | none* | 12.9 | 15.9 |
| | Biopectinase | S. cerevisiae | 0.88 | 1.24 |

EXAMPLE 32

10 g of gum talha was crushed, then dissolved in 90 ml of distilled water. 1.5 ml of an enzyme having rhamnosidase activity (Biopectinase L, ex Biocon U.K.,Ltd) was added and the resulting solution was stirred at room temperature for 68 hours, after which time rhamnose equivalent to 3.2 g rhamnose per 100 g (35.5% of the theor. yield) per 100 g gum talha. Some other sugars, had also been liberated into solution.

We claim:

1. A process for preparing L-rhamnose comprising the steps of:
   i) treating plant material containing glycosides having rhamnose in a terminal position with an enzyme combination comprising plant structural material degrading eznymes and a naringinase having a higher rhamnosidase than beta-glucosidase activity;
   (ii) removing flavones and flavone glycosides; and
   (iii) removing glucose.

2. A process according to claim 1 which includes the step of separation of insoluble solids after treatment with the enzyme combination.

3. A process according to claim 1 wherein the enzyme combination comprises one or more of protease, lipase, cellulase, hemicellulase and pectinase.

4. A process according to claim 1 wherein the glucose is removed by one or more process steps chosen from:
   i) selectively fermenting out glucose with a microorganism capable of converting glucose to alcohol;
   (ii) selectively enzymatic oxidation of glucose to gluconic acid and precipitating gluconic acid as its calcium salt;
   (iii) selective oxidation of glucose to 5-keto-gluconic acid with a suitable microorganism, from solutions containing no more than 7% (w/v) of glucose; and
   (iv) selective adsorbtion/absorbtion of glucose.

5. A process according to claim 1 wherein the plant material is crude citrus material or citrus waste.

6. A process according to claim 5, characterized in that the crude citrus material is derived from unripe citrus fruit.

7. A process according to claim 1, characterized in that the glycoside having rhamnose in a terminal position is selected from the group consisting of naringin, quercitrin, rutin, microbial rhamnolipids, microbial rhamnopolysaccharides and gum acacia.

8. A process according to claim 1, characterized in that the rhamnosidic bond of the glycoside is hydrolysed for a period of between 30 minutes and 36 hours.

9. A process according to claim 1, characterized in that the rhamnosidic bond of the glycoside is hydrolysed at a temperature between 20° and 60° C.

10. A process according to claim 1, characterized in that the rhamnosidic bond of the glycoside is hydrolysed in a pH range between 2 and 8.

11. A process according to claim 1, characterized in that the rhamnosidic bond of the glycoside is hydrolysed and any glucose in a hydrolysate obtained is removed by chemical or biochemical oxidation.

12. A process according to claim 1, characterized in that the rhamnosidic bond of the glycoside is hydrolysed, following which the hydrolysate is purified and glucose is removed.

13. A process according to claim 12, characterized in that enzymic hydrolysis and glucose removal are carried out simultaneously.

* * * * *

UNITED STATES PATENT AND TRADEMARK OFFICE
CERTIFICATE OF CORRECTION

PATENT NO. : 5,077,206

DATED : December 31, 1991

INVENTOR(S) : Cheetham et al

It is certified that error appears in the above-identified patent and that said Letters Patent is hereby corrected as shown below:

Column 1, line 53: the comma between "citrus" and "material" should be removed;

Column 2, lines 42: "buloaris" should be --bulgaris--;

Column 3, line 21: "or" should be --of--;

Column 6, line 4: "eznymes" should be --enzymes--;

Column 6, line 20: "selectively" should be --selective--.

Signed and Sealed this

Twentieth Day of April, 1993

Attest:

MICHAEL K. KIRK

*Attesting Officer*     *Acting Commissioner of Patents and Trademarks*